United States Patent [19]

Hobbs et al.

[11] 4,120,901
[45] Oct. 17, 1978

[54] PRODUCTION OF PRIMARY AND SECONDARY AMINES BY REACTION OF AMMONIA WITH CONJUGATED DIENE IN THE PRESENCE OF Pd/PHOSPHINE CATALYST AND PRIMARY OR SECONDARY ALIPHATIC ALCOHOL SOLVENT MEDIUM

[75] Inventors: Charles F. Hobbs, Des Peres; Dudley E. McMackins, St. Charles, both of Mo.

[73] Assignee: Monsanto Company, St. Louis, Mo.

[21] Appl. No.: 829,558

[22] Filed: Aug. 31, 1977

[51] Int. Cl.² .............................................. C07C 85/18
[52] U.S. Cl. ........................... 260/585 D; 252/431 C; 252/431 N; 252/431 P; 260/583 H
[58] Field of Search .......... 260/585 D, 583 H, 585 R; 252/431 C, 431 N, 431 P

[56] References Cited

FOREIGN PATENT DOCUMENTS 617,347  2/1949  United Kingdom ................ 260/585 D

OTHER PUBLICATIONS

Takahashi et al., "Bull. Chem. Soc. Jap.", vol. 45, pp. 1183–1191 (1972).

Primary Examiner—Winston A. Douglas
Assistant Examiner—John J. Doll
Attorney, Agent, or Firm—Scott J. Meyer; James W. Williams, Jr.

[57] ABSTRACT

Short chain, unsaturated primary and secondary amines are prepared by reaction of ammonia and conjugated dienes in a primary or secondary aliphatic alcohol solvent medium and in the presence of a catalyst system comprising a palladium compound co-catalyzed with a phosphine ligand containing 2 to 4 phosphorus atoms.

9 Claims, No Drawings

PRODUCTION OF PRIMARY AND SECONDARY AMINES BY REACTION OF AMMONIA WITH CONJUGATED DIENE IN THE PRESENCE OF PD/PHOSPHINE CATALYST AND PRIMARY OR SECONDARY ALIPHATIC ALCOHOL SOLVENT MEDIUM

BACKGROUND OF THE INVENTION

This invention relates to the palladium-catalyzed amination of conjugated dienes with ammonia to produce relatively short chain unsaturated primary and secondary amines.

Organic amines find a wide range of commercial usage such as paper and rubber chemicals, plasticizer intermediates, herbicide intermediates, surfactants, water treatment chemicals and extractants. Because prior methods of preparation are multi-step and sometimes non-selective, amines are a relatively expensive class of chemicals.

The direct addition of ammonia or amines to olefins is a potentially lower cost method of preparing amines. However, such direct addition has been hindered by the high reaction temperatures necessary to meet the activation energy requirements of the reaction and the unfavorable equilibrium thermodynamics for the reactions at these temperatures. One method of overcoming these obstacles is to find a catalyst to lower the energy of activation required and thus allow the reaction to proceed at temperatures where the equilibrium is more favorable.

Direct amination of olefins with amines using soluble palladium catalysts has been reported heretofore by several investigators, for example, Takahashi, Bull. Chem. Soc. Japan 41, 454–60 (1968) and in U.S. Pat. Nos. 3,350,451; 3,444,202; 3,530,187; and British Patent No. 1,178,812. However, the disclosed reactions do not involve ammonia itself and thus do not have the potential for producing primary amines as distinguished from secondary and tertiary amines.

Tsuji and co-workers reported the use of a palladium catalyst system which gives amination of butadiene with ammonia, Chem. Comm. (Japan), 345 (1971). The reaction is described as taking place in acetonitrile solvent and in the presence of palladium acetate and triphenyl phosphine. However, in the hands of the present inventors, the Tsuji reaction gave only low yields at slow rates.

Recently, in application Ser. No. 697,900, filed June 21, 1976, the present inventors disclosed an improved homogeneous palladium-based catalyst system which facilitates the amination of butadiene with either ammonia or amines with excellent yields and rates under mild conditions. These catalysts, however, give long chain secondary and tertiary octadienyl amines as a result of multiple alkylation of ammonia and telomerization of butadiene. The relatively shorter chain butenylamines desired herein were not produced by the catalyst system.

Preparation of the shorter chain butenylamines by reaction of primary and secondary amines with butadiene using a preformed palladium-diphosphine complex catalyst has been described by Takahashi et al., Bull. Chem. Soc. Japan 45, 1183–91 (1972). However, the reactivity of the amine reactants is reported to be associated with the amine basicity, with the more strongly basic amines being more active. No disclosure of the more weakly basic ammonia is provided by Takahashi. Moreover, the Takahashi reaction requires use of a co-catalytic amount of phenol to provide a suitable reaction rate.

BRIEF SUMMARY OF THE INVENTION

In accordance with the present invention, short chain primary and secondary unsaturated amines are produced by reaction of ammonia and conjugated dienes in a primary or secondary aliphatic alcohol solvent medium and in the presence of a catalyst comprising a palladium compound co-catalyzed with a phosphine ligand containing from 2 to 4 phosphorus atoms.

DETAILED DESCRIPTION OF THE INVENTION

The novel palladium-based catalyst system of this invention comprises a palladium compound co-catalyzed with a phosphine ligand containing from 2 to 4 phosphorus atoms such as a bidentate or tridentate ligand.

The preferred palladium compounds are salts with readily displaceable anions such as, for example, acetate, nitrate, cyanide and acetylacetonate. The most preferred of these is palladium acetate. It will be appreciated that mixtures of these and other such palladium compounds also can be used. Salts with strongly bound anions such as $Cl^-$ or $Br^-$ are substantially less effective in the catalyst system of this invention.

The preferred ligands employed in this invention are alkyl-, aryl-, and arylalkyl phosphines containing from two to four phosphorus atoms. Aralkyl compounds, especially arylalkyl phosphines containing alkyl or alkenyl chains of from two to four carbons separating the phosphorus atoms are most preferred. Specific examples of these compounds are:

1,2-bis(diphenylphosphino)ethane,
1,3-bis(diphenylphosphino)propane,
1,4-bis(diphenylphosphino)butane,
1,2-bis(diphenylphosphino)ethylene,
2,3-O-isopropylidene-2,3-dihydroxy-1,4-bis(diphenylphosphino)butane,
1,2-bis(O-anisylphenylphosphino)ethylene,
2,3-bis(diphenylphosphino)-2,3-dimethylbutane,
1,1,1-tris(diphenylphosphinomethyl)ethane, and
bis(2-diphenylphosphinoethyl)phenylphosphine.

The amount of ligand used can vary somewhat but best results are obtained with a phosphorus/palladium mole ratio of about 2 to 4. The preferred ratio is about 2.9. In various examples of the invention, increasing the ligand/palladium ratio gave slightly faster reaction rates with the tridentate ligand in contrast to the slower rates observed with higher ligand/palladium ratios using the bidentate 1,2-bis(diphenylphosphino)ethane. Arsine ligands are substantially less effective than the foregoing phosphino ligands.

Examples of conjugated dienes which can be appropriately aminated with ammonia by the aforesaid catalyst system of this invention are compounds having from four to about eight carbon atoms and containing conjugated double bonds, for example, 1-3-butadiene, isoprene, 1,3-pentadiene, 2,4-hexadiene, 2,3-dimethylbutadiene and the like compounds. Amination of 1,3-butadiene is preferred.

The mole ratio of ammonia to conjugated diene used in the palladium catalyzed reaction of this invention can vary widely, for example, from about 1:3 to about 24:1. The preferred range is from about 3:1 to about 12:1.

It has been found that the use of a primary or secondary aliphatic alcohol solvent medium for the disclosed catalyst system is important for obtaining high yields of product. The preferred aliphatic alcohols have from 1 to 10 carbon atoms. Illustrative of such solvents are methanol, ethanol, propanol, isopropanol, butanol, hexanol, cyclohexanol, octanol and decanol.

Although the inventors are not to be bound by theory, it is believed that the primary or secondary aliphatic alcohol solvent must be present in an amount sufficient to reduce the palladium from the divalent to the zerovalent state as shown in the following illustrative reaction:

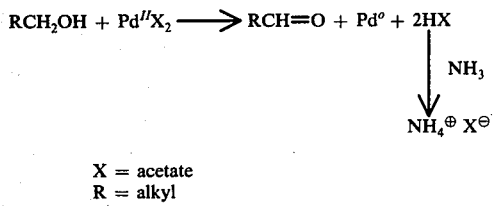

X = acetate
R = alkyl

By way of comparison, the heretofore disclosed phenol does not provide the necessary aliphatic hydrogens for such reaction.

Reaction temperatures can vary from about 50° C. to about 200° C., but the preferred range is from about 100° C. to about 145° C.

Addition of trifluoroacetic acid to the reaction mixture, while not necessary to the invention, increases the rate of reaction. It thereby enables the carrying out of the reaction at lower temperatures with better reaction rates than those obtained when no acid is used. For example, addition of about 0.005 mole of ammonium trifluoroacetate to about one-half mole of reactants (six parts butadiene to one part ammonia) allowed the palladium-catalyzed reaction to be run at 100° C. vs. the 145° C. preferred when run without the ammonium trifluoroacetate.

The primary amines obtained by the novel process of this invention can be represented by the general structure

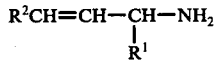

wherein $R^1$ and $R^2$ can be hydrogen or alkyl radicals of from one to four carbon atoms, such as methyl, ethyl, propyl, isopropyl and butyl.

The secondary amines can be represented by the general structure

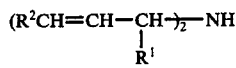

wherein $R^1$ and $R^2$ are as stated above.

The chain length in these primary and secondary amines is the same as the chain length in the reactant conjugated diene.

The products of the palladium catalyzed reaction using, for example, 1,3-butadiene as the diene are predominately primary butenylamines, with lesser amounts of secondary butenylamines, although the reaction can easily be modified to produce predominately the latter. The primary butenylamines consist of 2- butenylamine and α-methallylamine having the structures:

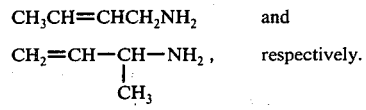

The amine products of the reactions of the invention are useful as acid scavengers, rubber and paper chemicals and, in their cationic form, as fungicides. They can also be copolymerized with acrylonitrile to give polymers having improved dye retention. These products also can be polymerized with other monomers through the amine function with the pendant ethylenic function and then reacted to produce a cross-linked polymer. The unsaturated ethylenic linkages in these products can be hydroxylated or hydrated to form useful alcohol derivatives from which esters or ethers are prepared. The ethylenic linkage can serve as a dienophile in Diels-Alder condensations and as an active site in polymerization processes. Hydrogenation of the ethylenic linkage also can occur to give saturated amines.

The following detailed examples with further illustrate the invention although it will be appreciated that the invention is not limited to these specific examples.

EXAMPLE 1

A reaction illustrating the invention was run in a 45-ml, stainless steel autoclave equipped with a stirrer and a pressure gauge. In the reaction, 1.67 grams (7.4 millimoles) of palladium acetate, 4.13 g of 1,2-bis(diphenylphosphino)ethane (DIPHOS) and 33 ml of ethanol were charged into the autoclave under a nitrogen atmosphere. A partial vacuum was applied to the autoclave which was cooled in a Dry Ice bath. Ammonia (54.4 g, 3.2 moles) and then 1,3-butadiene (28.7 g, 0.53 mole) were condensed into the autoclave from calibrated reservoirs. The reaction mixture was heated to 145° C. and stirred for one hour during which time the autogenous pressure dropped from approximately 1100 psig to 1000 psig. The liquid product was filtered from the solid catalyst residue (about one gram) and then distilled at reduced pressure through a short-path head to separate it from any dissolved catalyst. This distillate was then fractionally distilled to separate the various products. Identification of products was made on the basis of VPC, proton nuclear magnetic resonance, VPC/mass spectroscopy and elemental analysis. VPC of the reaction product showed that 90% of the butadiene had been converted to a mixture of monobutenyl amines (49%), dibutenyl amines (27%), tributenyl amines (8%), a trace of $C_{16}$ amine, and butadiene dimers (16%). The monobutenyl amines consisted of α-methallylamine (62%), trans-2-butenylamine (30%), and cis-2-butenylamine (8%). The dibutenylamines consisted of N-2-butenyl-α-methallylamine (about 50%), bis(2-butenyl)amine (50%), and a trace of bis(α-methallyl)amine. Boiling points and elemental analysis are shown in the following Table I:

TABLE I
Product Boiling Points and Elemental Analysis Data

| Compound | Boiling Point °C, mm Hg | Elemental Analysis, Cald'd (Found) C | H | N |
|---|---|---|---|---|
| ⟩—NH₂ | 61-62(750) | 67.55(67.55) | 12.75(12.75) | 19.67(19.70) |
| ⟋⟍⟋—NH₂ | 81-82(750) | 67.55(67.55) | 12.78(12.75) | 19.66(19.70) |
| 36% ⟍⟋—NH₂ + 64% ⟋⟍⟋—NH₂* | 84-85(750) | 67.35(67.55) | 12.81(12.75) | 19.73(19.70) |
| ⟩—N(H)—⟍⟋ | 142-144(750) | 76.66(76.74) | 12.07(12.07) | 11.16(11.19) |
| ⟋⟍⟋—N(H)—⟍⟋ | 74(27) | 76.73(76.74) | 12.05(12.07) | 11.07(11.19) |

*isomer ratio determined by VPC.

In the following Examples 2 through 10, essentially the same procedure, conditions and reactants as in Example 1 were employed except that various other bidentate or tridentate ligands were substituted for the DIPHOS in the catalyst system in Example 1. The percent butadiene converted to the various amine products is set forth in the following Table II:

diphosphine complex, $PdBr_2(Ph_2PCH_2CH_2PPh_2)_2$, where Ph=phenyl, with sodium phenoxide and phenol has been disclosed heretofore as an effective catalyst system for the reaction of amines with butadiene. In test A, below, this palladium-based catalyst system containing the bromide anion and a phenolic co-catalyst was found ineffective for the production of monobutenyla-

TABLE II
Effect of Ligand Structure
$C_4H_6 + NH_3 + Pd(OAc)_2 + $ Ligand $ + $ EtOH; 1 hr, 145° C

| | | | % $C_4H_6$ Converted to: | | | | | | | |
|---|---|---|---|---|---|---|---|---|---|---|
| Ex. No. | Ligand | Charged Ammonia Butadiene mole ratio | α-methallyl-amine | 2-butenyl-amine | Total Mono-butenyl Amines | Di-butenyl Amines | $C_{12}$ Amines | Total Amines | Monobutenyl Amines Total Amines | Butadiene Oligomers |
| | Bidentate Ligands: | | | | | | | | | |
| 2 | φ₂PCH₂Pφ₂ | 6 | 9 | 4 | 12 | 13 | 4 | 48ᵃ | .25 | 34 |
| 3 | φ₂P(CH₂)₂Pφ₂ (DIPHOS) | 6 | 27 | 17 | 44 | 24 | 7 | 76 | .58 | 9 |
| 4 | φ₂P(CH₂)₃φ₂ | 6 | 25 | 26 | 51 | 34 | 5 | 90 | .57 | 6 |
| 5 | φ₂P(CH₂)₄Pφ₂ | 6 | 27 | 11 | 38 | 18 | 11 | 69 | .55 | 23 |
| 6 | cis-φ₂PCH=CHPφ₂ | 6 | 40 | 8 | 48 | 15 | 1 | 68 | .71 | 5 |
| 7 | φ₂PC≡CPφ₂ᵇ | 6 | 7 | 0 | 7 | 4 | 0 | 12 | .58 | 15 |
| 8 | (DIOP structure) | 6 | 29 | 9 | 38 | 19 | 8 | 69 | .55 | 22 |
| | Tridentate Ligands: | | | | | | | | | |
| 9 | CH₃C(CH₂Pφ₂)₃ᵇ | 6 | 39 | 14 | 54 | 26 | 2 | 82 | .66 | 11 |
| 10 | φ₂P(CH₂)₂Pφ(CH₂)₂Pφ₂ (TRIPHOS) | 1 | 5 | 0 | 5 | 4 | 14 | 43ᵃ | .12 | 14 |
| | φ₂P(CH₂)₂Pφ₂ (DIPHOS) (for comparison) | 1 | 10 | 6 | 16 | 22 | 15 | 58 | .39 | 13 |

ᵃIncludes significant conversion to $C_{16}$ and $C_{20}$ amines.
ᵇGave almost completely homogenous products.

EXAMPLE 11

Example 1 was essentially repeated except that butanol was substituted for ethanol with substantially similar total conversion and product distribution.

EXAMPLE 12

Butadiene (0.48 mole), ammonia (0.08 mole), palladium acetate (1.1 mmol), DIPHOS (1.6 mmol), 0.005 mmol ammonium trifluoroacetate and 5 ml of ethanol were reacted for 1 hour at 100° C. in a manner similar to that of Example 1. The conversion to amines was 36% (based on butadiene).

In order to further demonstrate the unique properties of the present catalyst system for the production of monobutenylamines by reaction of ammonia with butadiene, a series of comparative tests were run in which prior art palladium bidentate-phosphine catalyst systems were substituted for the present catalyst system. Thus, the combination of the preformed palladiummines by reaction of ammonia with butadiene.

Use of palladium acetate and a bidentate-phosphine ligand, $Ph_2PCH_2CH_2PPh_2$, also has been described heretofore as effective for the reaction of active hydrogen compounds with butadiene. In tests B, C and D, below, this catalyst by itself was found to be relatively ineffective for the production of monobutenylamines by reaction of ammonia and butadiene.

Use of phenol has been reported heretofore to enhance the catalytic activity of the reaction of amines and butadiene using palladium acetate and $Ph_2PCH_2CH_2PPh_2$ ligand. However, when ammonia was reacted with butadiene using the catalytic system of the present invention as shown in tests E and F below, no enhancement in the production of the desired monobutenylamines was obtained by the added presence of phenol.

Test A

When ammonia (0.1 mole), 1,3-butadiene (0.15 mole), bis[1,2-bis(diphenylphosphino)ethane] palladium dibromide (0.25 mmole), sodium phenate (2.5 mmoles) and phenol (2.5 mmoles) were heated for 1 hour at 145° C., less than 5% of the ammonia was converted to monobutenylamines, while at least 37% of the butadiene was converted to butadiene dimers. Approximately 2% of the ammonia was converted to $C_8$ to $C_{16}$ amines.

Test B

When ammonia (0.48 mole), 1,3-butadiene (0.08 mole), palladium acetate (1.1 mmole), and 1,2-bis(diphenylphosphino)ethane (2.78 mmoles) were heated above 135° C., the pressure generated could not be contained, the temperature being higher than the critical temperature of ammonia. When the above reactants were heated for 1 hour at 128° C., no monobutenylamines were detected in the product. 2.6% of the butadiene had been converted to dibutenylamines while 0.1% had been converted to $C_{12}H_{21}N$ amines.

Test C

When ammonia (0.1 mole), 1,3-butadiene (0.15 mole), palladium acetate (1.1 mmole), and 1,2-bis(diphenylphosphino)ethane (2.78 mmoles) were heated for one hour at 145° C., no monobutenylamines and only traces of dibutenylamines were found. 0.8% of the ammonia was converted to $C_{12}H_{21}N$-amines. 4.3% of the butadiene was converted to butadiene dimers.

Test D

When ammonia (0.1 mole), 1,3-butadiene (0.15 mole), palladium acetate (1.1 mmole) and 1,2-bis(diphenylphosphino)ethane (0.28 mmole) were heated for one hour at 145° C., no monobutenylamines were detected. Only traces of $C_8$ to $C_{12}$ amines were seen while 58% of the butadiene was converted into a mixture of butadiene oligomers.

Test E 0.25 gram (1.1 millimole) of palladium acetate, 0.62 gram (1.6 millimole) of 1,2-bis(diphenylphosphine)ethane, 8.16 grams (0.48 mole) of ammonia and 4.3 grams (0.08 mole) of 1,3-butadiene were stirred in 5 ml. of ethanol for one hour at 1.45° C. VPC of the reaction product showed that 27% of the butadiene had been converted to α-methallylamine, 17% to 2-butenylamine, 24% to dibutenylamines, 7% to tributenylamines and 17% to butadiene oligomers.

When the above reaction was carried out in the added presence of 0.1 gram (1.1 millimole) of phenol, VPC of the reaction product showed that 28% of the butadiene had been converted to α-methallylamine, 16% to 2-butenylamine, 18% to dibutenylamines, 4% to tributenylamines and 9% to butadiene oligomers.

When the same reaction was carried out in the added presence of 0.4 gram (4.4 millimoles) of phenol, VPC of the reaction product showed that 27% of the 1,3-butadiene had been converted to α-methallylamine, 19% to 2-butenylamine, 19% to dibutenylamines, 2% to tributenylamines and 9% to butadiene oligomers.

Test F 0.25 gram (1.1 millimole) of palladium acetate, 0.62 gram (1.6 millimole) of 1,2-bis(diphenylphosphino)ethane, 1.12 gram (0.08 mole) of ammonia, and 13.0 grams (0.24 mole) of 1,3-butadiene were stirred in 5 ml of ethanol for 15 minutes at 145° C. VPC of the reaction product showed that 28% of the ammonia had been converted to α-methyallylamine, 14% to dibutenylamines, 21% to tributenylamines, 12% to $C_{12}$ amines and 3% to $C_{20}$ amines.

When the above reaction was carried out in the presence of 0.1 gram (1.1 millimole) of phenol, VPC of the reaction product showed that 20% of the ammonia had been converted to α-methallylamine, 18% to dibutenylamines, 29% to tributenylamines, 16% to $C_{16}$ amines and 4% to $C_{20}$ amines.

Various other examples will be apparent to the person skilled in the art after reading the present diclosure without departing from the spirit and scope of the invention. All such other examples are included within the scope of the appended claims.

What is claimed is:

1. The process of reacting ammonia with a conjugated diene having from 4 to 8 carbon atoms in a solvent reaction medium consisting essentially of one or more alcohols selected from the group consisting of primary and secondary aliphatic alcohols and in the presence of a catalyst system consisting essentially of a palladium compound with a phosphine ligand containing from 2 to 4 phosphorus atoms to thereby produce an unsaturated amine product selected from the group consisting of secondary and primary amines.

2. The process of claim 1 in which the conjugated diene is butadiene.

3. The process of claim 1 in which the aliphatic alcohol is ethanol.

4. The process of claim 1 in which the ligand is an arylalkyl phosphine containing an alkyl or alkenyl chain of from 2 to 4 carbons separating the phosphorus atoms.

5. The process of claim 4 in which the ligand is 1,2-bis(diphenylphosphino)ethane.

6. The process of claim 1 in which the palladium compound is palladium acetate.

7. The process of claim 1 in which trifluoroacetic acid is employed as an additional component in the reaction medium to thereby allow the reaction to be carried out at a reduced temperature.

8. The process of claim 1 in which ammonia is reacted with butadiene in the presence of ethanol solvent and a catalyst system comprising palladium acetate and 1,2-bis(diphenylphosphino)ethane to thereby produce an amine product selected from the group consisting of 2-butenylamine, α-methallylamine and mixtures thereof.

9. The process of claim 1 in which ammonia is reacted with the conjugated diene at a temperature ranging from about 50° C. to about 200° C.

* * * * *